(12) United States Patent
Murayama (10) Patent No.: US 8,049,803 B2
(45) Date of Patent: Nov. 1, 2011

(54) SOLID STATE IMAGE PICKUP DEVICE AND ENDOSCOPE

(75) Inventor: Jin Murayama, Kurokawa-gun (JP)

(73) Assignee: FUJIFILM Corporation, Tokyo (JP)

( * ) Notice: Subject to any disclaimer, the term of this patent is extended or adjusted under 35 U.S.C. 154(b) by 1287 days.

(21) Appl. No.: 11/483,084

(22) Filed: Jul. 10, 2006

(65) Prior Publication Data

US 2007/0012954 A1 Jan. 18, 2007

(30) Foreign Application Priority Data

Jul. 14, 2005 (JP) ................... 2005-205820

(51) Int. Cl.
*H04N 5/335* (2011.01)
*H01L 29/18* (2006.01)
*H01L 29/768* (2006.01)

(52) U.S. Cl. .................. 348/311; 257/88; 257/222

(58) Field of Classification Search .............. 348/311; 257/88, 222
See application file for complete search history.

(56) References Cited

U.S. PATENT DOCUMENTS

| 7,365,379 B2 * | 4/2008 | Murayama et al. ........... 257/291 |
| 7,515,185 B2 * | 4/2009 | Nakamura et al. ........... 348/294 |

| 2002/0020845 A1 | 2/2002 | Ogura et al. |
| 2002/0032367 A1 | 3/2002 | Akiba |
| 2003/0230147 A1 * | 12/2003 | Stratton et al. ........... 73/727 |

FOREIGN PATENT DOCUMENTS

| EP | 1 180 345 A2 | 2/2002 |
| JP | 11-295620 | 10/1999 |
| JP | 2004-006834 A | 1/2004 |

OTHER PUBLICATIONS

EP Communication, dated Sep. 1, 2009, issued in corresponding EP Application No. 06253418.5, 6 pages.

* cited by examiner

*Primary Examiner* — Kelly L Jerabek
*Assistant Examiner* — Joel Fosselman
(74) *Attorney, Agent, or Firm* — Sughrue Mion, PLLC (57) ABSTRACT

A solid state image pickup device includes: a semiconductor substrate; a well formed in a surface layer of the semiconductor substrate; a light reception region formed in the well and including a plurality of charge accumulation regions formed in a matrix shape and a plurality of vertical CCDs formed along each column of the charge accumulation regions; a horizontal CCD formed in the well and coupled to ends of the vertical CCDs; a peripheral circuit formed in the well in partial regions of the light reception region and the horizontal CCD; a shield layer formed on the semiconductor substrate including a partial area above the peripheral circuit, made of conductive material and surrounding the light reception region, the shield layer being electrically connected to the semiconductor substrate; a support disposed above the shield layer and made of conductive material; and a translucent member placed on the support.

20 Claims, 9 Drawing Sheets

SOLID STATE IMAGE PICKUP DEVICE AND ENDOSCOPE

CROSS REFERENCE TO RELATED APPLICATION

This application is based on and claims priority of Japanese Patent Application No. 2005-205820 filed on Jul. 14, 2005, the entire contents of which are incorporated herein by reference.

BACKGROUND OF THE INVENTION

1. A) Field of the Invention

The present invention relates to a solid state image pickup device and an endoscope using a solid state image pickup device.

1. B) Description of the Related Art

Various structures and manufacture methods are known for a solid state image pickup device (semiconductor chip) whose light reception region is protected with a protective glass (e.g., refer to Japanese Patent Laid-open Publication No. 2004-6834).

FIGS. 7A to 7G are schematic cross sectional views illustrating a solid state image pickup device using a wafer level chip size packaging (CSP) process.

Figure 7A:
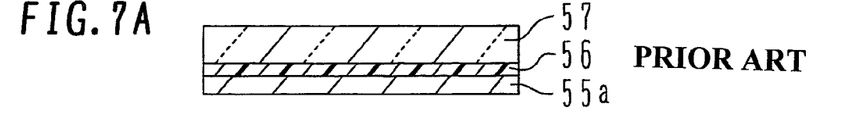
FIGS. 7A to 7G are schematic cross sectional views illustrating a solid state image pickup device manufacture method using a wafer level CSP process.

Reference is made to FIG. 7A. A protective glass 57 and a silicon substrate 55a are bonded together with adhesive 56 of, for example, an ultraviolet ray curing type. Spacers are formed by using the silicon substrate 55a in the next process.

Figure 7B:
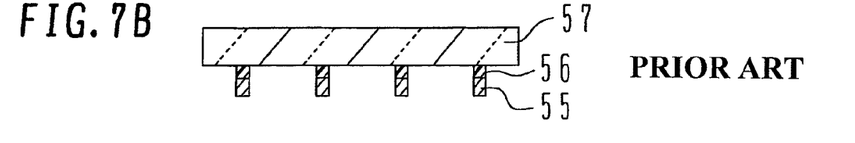

Reference is made to FIG. 7B. Resist patterns are formed on the silicon substrate 55a by photolithography in the areas where spacers are to be formed. The silicon substrate 55a is then etched to form spacers 55.

Figure 7C:
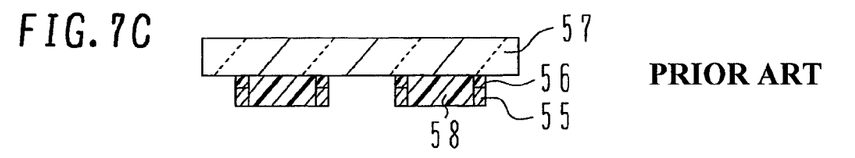

Reference is made to FIG. 7C. The regions between spacers 55 excepting the regions between devices are filled with resist 58, and the protective glass 57 is etched to a predetermined depth.

Figure 7D:
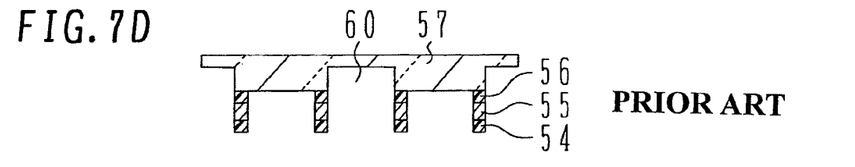

Reference is made to FIG. 7D. The etched region of the protective glass 57 constitutes an inter-device groove 60. Adhesive 54 of, for example, a thermosetting type is coated on the bottoms of the spacers 55. With the processes shown in FIGS. 7A to 7D, a sealing cover glass is formed.

Figure 7E:
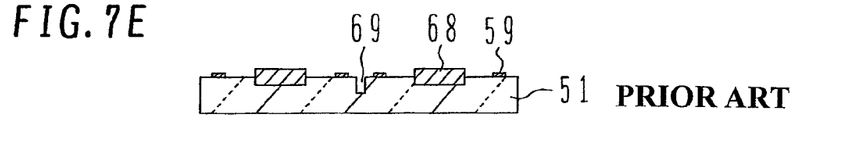

Reference is made to FIG. 7E. Next, a solid state image pickup device substrate is formed.

First, a cut groove 69 is formed in the surface layer of the silicon substrate 51 by etching or the like, in the area corresponding to a dicing line for separating the substrate into each semiconductor chip. Next, a solid state image pickup device 68 is formed by ordinary silicon processes. A wiring layer is formed on the substrate surface, and pads 59 of metal material for external connection are formed.

Figure 7F:
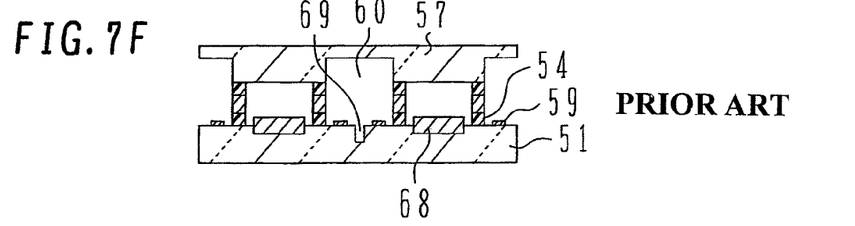

Reference is made to FIG. 7F. Position alignment is performed and the sealing cover glass is placed on the solid state image pickup device substrate. The sealing glass cover and substrate are integrally bonded with heated adhesive 54. This process is preferably executed in a vacuum state, a nitrogen gas atmosphere or an inert gas atmosphere, or in an atmosphere of nitrogen gas or inert gas mixed with some air.

Figure 7G:
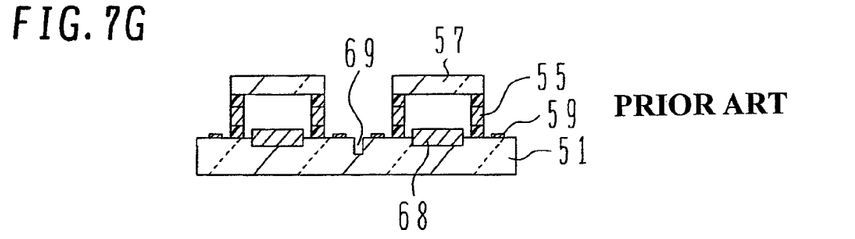

Reference is made to FIG. 7G. The upper side of the protective glass 57 is removed down to the inter-device groove 60 by chemical mechanical polishing (CMP). The bottom side of the silicon substrate is removed up to the cut groove 69 by CMP to separate the substrate into each semiconductor chip.

SUMMARY OF THE INVENTION

An object of this invention is to provide a solid state image pickup device having high resistance against electrostatic breakdown.

Another object of this invention is to provide an endoscope having high resistance against electrostatic breakdown.

According to one aspect of the present invention, there is provided a solid state image pickup device comprising: a semiconductor substrate of a first conductivity type; a well of a second conductivity type opposite to the first conductivity type formed in a surface layer of the semiconductor substrate; a light reception region formed in the well and including a plurality of charge accumulation regions of the first conductivity type formed in a matrix shape for accumulating signal charges generated in correspondence with an amount of incidence light and a plurality of vertical CCDs formed along each column of the charge accumulation regions for reading the signal charges accumulated in the charge accumulation regions and transferring the signal charges in a column direction; a horizontal CCD formed in the well and coupled to ends of the vertical CCDs for transferring the signal charges transferred from the vertical CCDs; a peripheral circuit formed in the well in partial regions of the light reception region and the horizontal CCD; a shield layer formed on the semiconductor substrate including a partial area above the peripheral circuit, made of conductive material and surrounding the light reception region, the shield layer being electrically connected to the semiconductor substrate of the first conductivity type; a support disposed above the shield layer and made of conductive material; and a translucent member placed on the support.

This solid state image pickup device has a high electrostatic breakdown resistance and high quality capable of preventing devices such as an input/output protective circuit and a wiring portion from being broken, even if a strong electric field is generated between the bottom surface of the support and the semiconductor substrate due to static electricity generated, for example, on the translucent member.

According to another aspect of the present invention, there is provided an endoscope comprising: a light source for emitting light; a solid state image pickup device including a semiconductor substrate of a first conductivity type, a well of a second conductivity type opposite to the first conductivity type formed in a surface layer of the semiconductor substrate, a light reception region formed in the well and including a plurality of charge accumulation regions of the first conductivity type formed in a matrix shape for accumulating signal charges generated in correspondence with an amount of incidence light and a plurality of vertical CCDs formed along each column of the charge accumulation regions for reading the signal charges accumulated in the charge accumulation regions and transferring the signal charges in a column direction, a horizontal CCD formed in the well and coupled to ends of the vertical CCDs for transferring the signal charges transferred from the vertical CCDs, a peripheral circuit formed in the well in partial regions of the light reception region and the horizontal CCD, a shield layer formed on the semiconductor substrate including a partial area above the peripheral circuit, made of conductive material and surrounding the light reception region, the shield layer being electrically connected to the semiconductor substrate of the first conductivity type, a support disposed above the shield layer and made of conductive material, and a translucent member placed on the support; and a transmission tube having therein the light source and the solid state image pickup device.

This endoscope using the above-described solid state image pickup device has a high quality and can prevent breakage of a device such as an input/output protective circuit and a wiring portion.

According to the present invention, it is possible to provide a solid state image pickup device having high resistance against electrostatic breakdown.

According to the present invention, it is possible to provide an endoscope having high resistance against electrostatic breakdown.

DESCRIPTION OF THE PREFERRED EMBODIMENTS

Figure 1A:
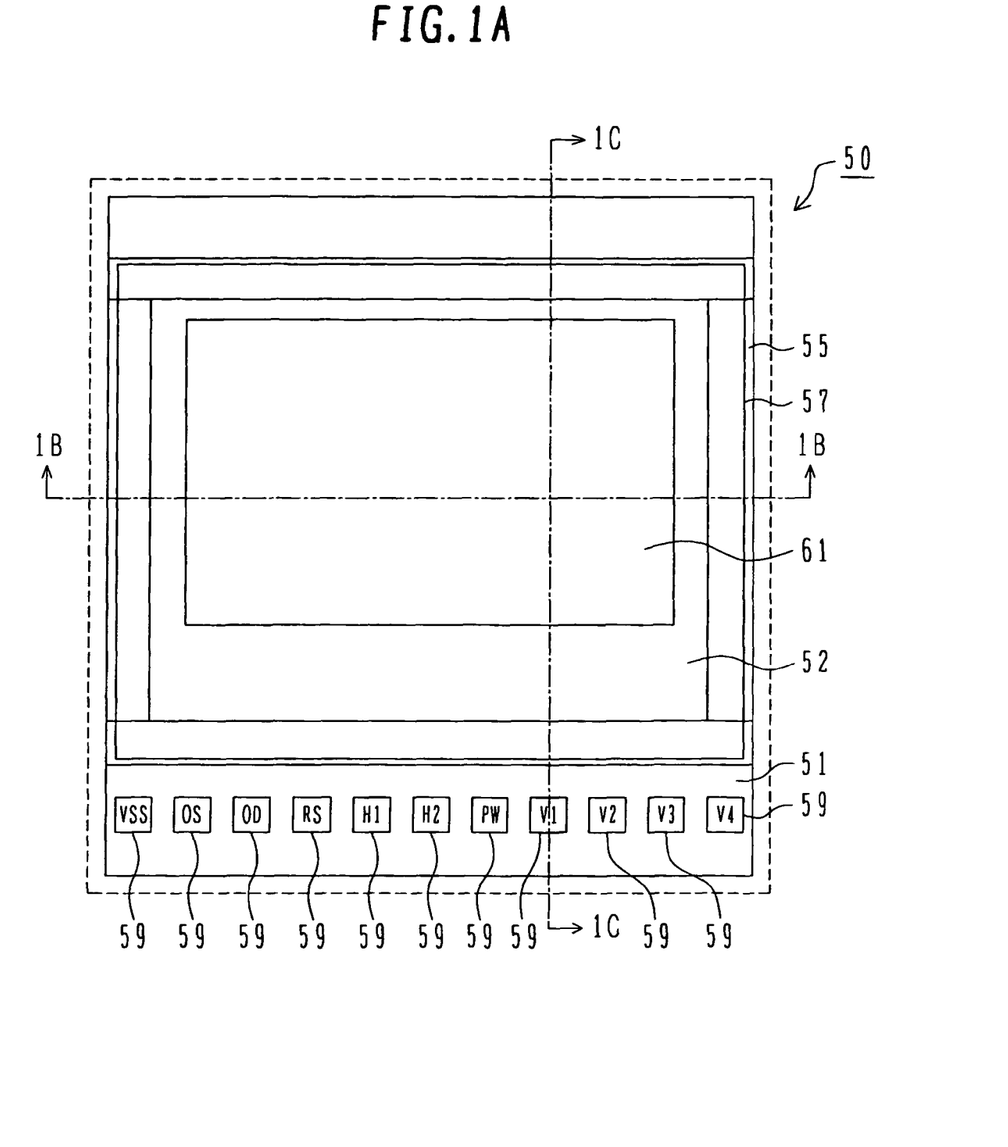
FIG. 1A is a schematic plan view showing an example of a semiconductor chip 50 formed with a solid state image pickup device whose light reception region is protected with a protective glass.
Figure 1B:
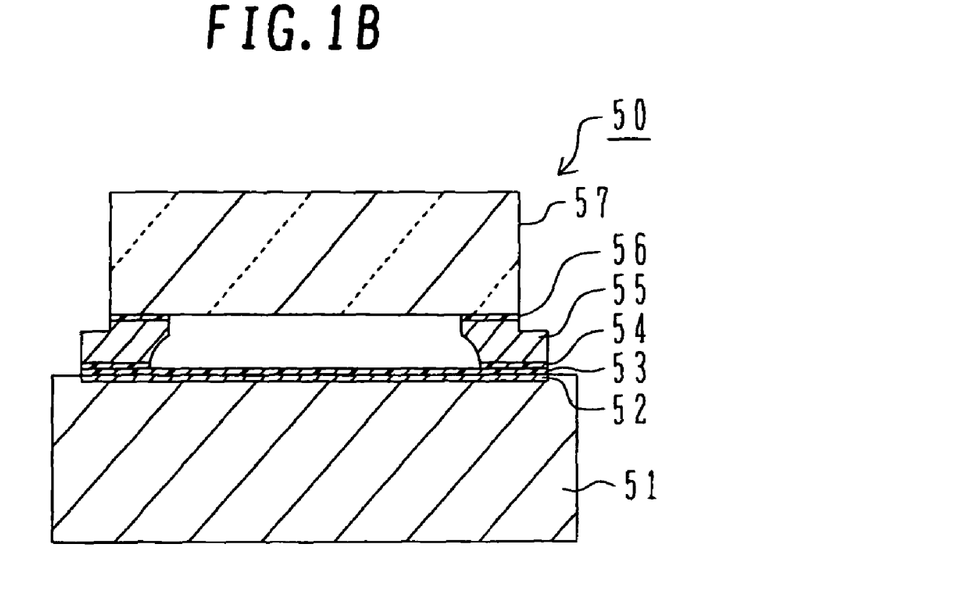
FIGS. 1B and 1C are cross sectional views taken along respective lines 1B-1B and 1C-1C shown in FIG. 1A.
Figure 1C:
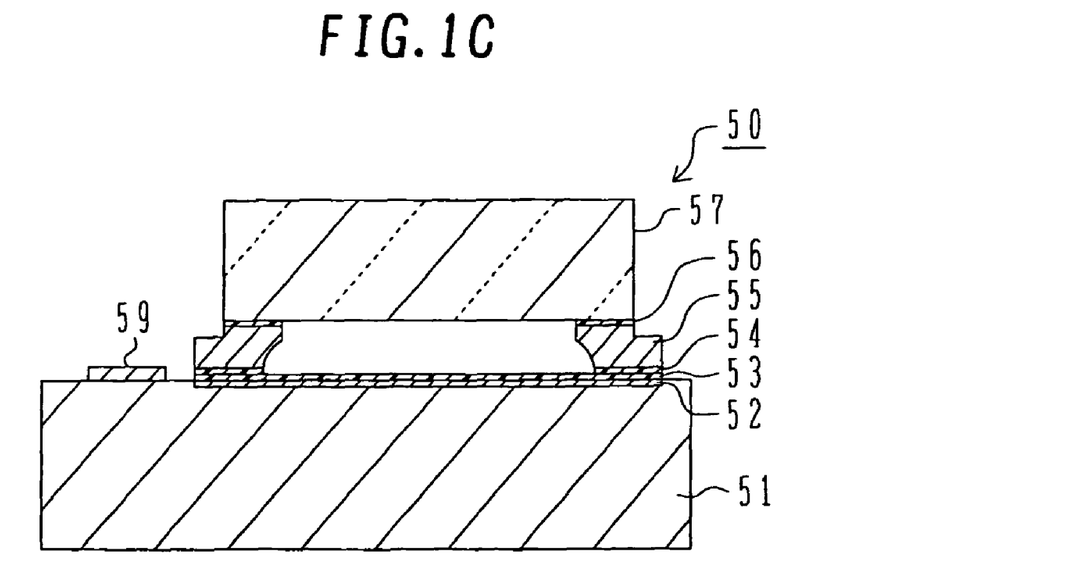

FIG. 1A is a schematic plan view showing an example of a semiconductor chip 50 formed with a solid state image pickup device whose light reception region is protected with a protective glass. FIGS. 1B and 1C are cross sectional views taken along respective lines 1B-1B and 1C-1C shown in FIG. 1A.

The semiconductor chip 50 includes a silicon substrate 51, a semiconductor device 52 formed on the silicon substrate 51, a spacer (support member) 55 formed on the semiconductor device 52, a protective glass 57 adhered to the spacer 55, and a plurality of pads 59 formed in the peripheral area of the silicon substrate 51.

The semiconductor device 52 includes a solid state image pickup device and its peripheral circuit (e.g., an input/output protective circuit for protecting an internal circuit from an external surge voltage, and a wiring portion such as outer peripheral wirings). For the purposes of simplicity, a portion formed near the surface of the silicon substrate 51 is called a semiconductor device 52.

The spacer 55 made of conductive material such as silicon is formed on the semiconductor device 52, with an insulating film being interposed therebetween. The spacer 55 is formed surrounding the outer periphery of the light reception region 61 of the solid state image pickup device, as viewed in plan.

A translucent member such as protective glass 57 is placed on the spacer 55. The protective glass 57 protects the solid state image pickup device from moisture and mechanical factors. The semiconductor chip 50 can be manufactured by forming a number of semiconductor devices 52 on a silicon wafer and dicing the wafer into separate semiconductor devices 52. Dust formed during the manufacture processes, especially during processes after the dicing process, is prevented from attaching the light reception region 61 by the protective glass 57.

Plural pads 59 are external connection terminals for electrical connection between the semiconductor chip 50 and a circuit board on which drive circuits, wirings and the like are formed.

Reference is made to FIG. 1B. The semiconductor device 52 is formed by processing the silicon substrate 51 through ion implantation and the like. A passivation film 53 having a thickness of, e.g., 2 µm, is formed on the semiconductor device 52. The spacer 55 having a thickness of, e.g., 100 µm, is bonded to the passivation film 53 with epoxy-resin based adhesive 54. A thickness of the adhesive 54 is, for example, 2 µm.

The protective glass 57 having a thickness of, e.g., 250 µm, is bonded to the spacer 55 with adhesive 56 of an ultraviolet curing type.

Reference is made to FIG. 1C. As described earlier, each pad 59 is used for electrical connection (wire bonding) between the semiconductor chip 50 and an external wiring substrate. Each pad 59 is formed at a position where a capillary of a bonder does not contact the protective glass 57 during wire bonding. This is because the protective glass 57 may be broken if the capillary contacts the protective glass 57. Therefore, the pad 59 is formed at the position spaced by a predetermined distance from the end of the protective glass 57.

In order to meet compactness requirements of the semiconductor chip 50, the present inventor has proposed various approaches (e.g., refer to claims and paragraphs [0041] to [0079] of Best Mode for Carrying Out the Invention in Specification of Japanese Patent Application No. 2004-183868). For example, a solid state image pickup device having a width of 2 mm and 0.17 million pixels was manufactured in order to narrowing a transmission tube of an endoscope. However, in order to realize compactness, the spacer 55 is formed above a partial region of the peripheral circuit (input/output protective circuit or the like, or a wiring portion such as outer peripheral wirings or the like). Some phenomena occurred such as malfunction of an input/output protective circuit or a wiring portion such as an outer peripheral wiring portion).

According to the studies by the present inventor, the input/output protective circuit and wiring portion are positioned lower than, for example, by 1 to 5 µm from the surface (uppermost surface) of the semiconductor device 52, and near at, for example, 2 to 10 µm from the bottom surface of the spacer 55.

When the semiconductor chip 50 having the structure that the light reception region 61 of the solid state image pickup device is covered with the protective glass 57 placed on the spacer 55 is to be manufactured, as described with reference to FIGS. 7A to 7G, in many cases, first the spacer 55 and protective glass 57 are bonded together and thereafter the protective glass 57 is bonded to the semiconductor device 52 via the spacer 55. These processes are performed relative to a silicon wafer, and each semiconductor chip 50 with the semiconductor device 52 is formed by dicing the wafer.

Static electricity is generated in some cases on the surface of the protective glass 57, during a bonding process for the spacer 55 and protective glass 57, during a bonding process for the spacer 55 bonded to the protective glass 57 and the semiconductor device 52 or during a dicing process.

As static electricity is generated on the surface of the protective glass 57, charges having an opposite polarity are generated on the bottom surface of the protective glass 57. Since the spacer 55 made of conductor exists between the bottom surface of the protective glass 57 and the semiconductor device 52, a strong electric field caused by the static electricity is generated in a narrow region from the bottom surface of the spacer 55 to the input/output protective circuit and wiring portion, for example, having a distance of 2 to 10 μm. The present inventor has considered that this strong electric field causes electrostatic breakage of the input/output protective circuit and wiring portion, resulting in a malfunction of circuit operation.

Malfunction of circuit operation is hard to occur in a widely used ceramic package. This may be ascribed to that a ceramic package has a distance of several hundred μm between the lower surface of the protective glass at the upper surface of the package and the input/output protective circuit and wiring portion on the semiconductor device. This distance causes an electric field due to static electricity to have an intensity weaker by about two digits than that of the semiconductor chip having the structure that the light reception region of the solid state image pickup device is covered with the protective glass placed on the spacer.

Based on these studies, the present inventor has devised a solid state image pickup device and an endoscope having a novel structure.

Figure 2:
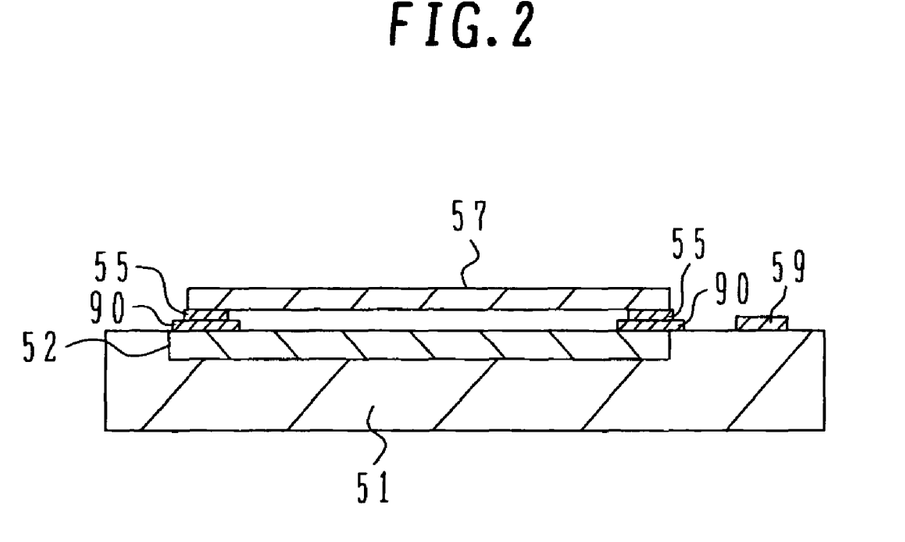
FIG. 2 is a schematic cross sectional plan view of a solid state image pickup device according to an embodiment.

FIG. 2 is a schematic cross sectional view of a solid state image pickup device according to an embodiment.

A semiconductor device 52 is formed on a silicon substrate 51. The semiconductor device 52 includes a solid state image pickup device and its peripheral circuit (e.g., an input/output protective circuit and a wiring portion such as outer peripheral wirings).

A spacer 55 made of, for example, Si, is disposed above the semiconductor device 52 via a shield layer 90 which is made of conductor such as aluminum (e.g., aluminum, or alloy of aluminum and copper or silicon containing aluminum as its main composition). The spacer 55 is disposed surrounding the periphery of the light reception region of the solid state image pickup device as viewed in plan (as the semiconductor device 52 is viewed from the position of the protective glass 57). Therefore, the shield layer 90 under the spacer 55 is also formed surrounding the periphery of the light reception region.

A translucent member, e.g., the protective glass 57, is placed on the spacer 55. Pads 59 are formed on the silicon substrate 51 for electrical connection to an external wiring substrate.

An insulating layer is formed between the semiconductor device 52 and shield layer 90 and between the shield layer 90 and spacer 55.

The shield layer 90 is electrically connected to the n-type silicon substrate 51 and is conductive to the bottom surface of the silicon substrate 51 at low resistance. The shield layer 90 and silicon substrate 51 (at the bottom surface thereof) have therefore generally the same potential.

The bottom surface of the silicon substrate 51 is electrically connected to an external apparatus.

Figure 3A:
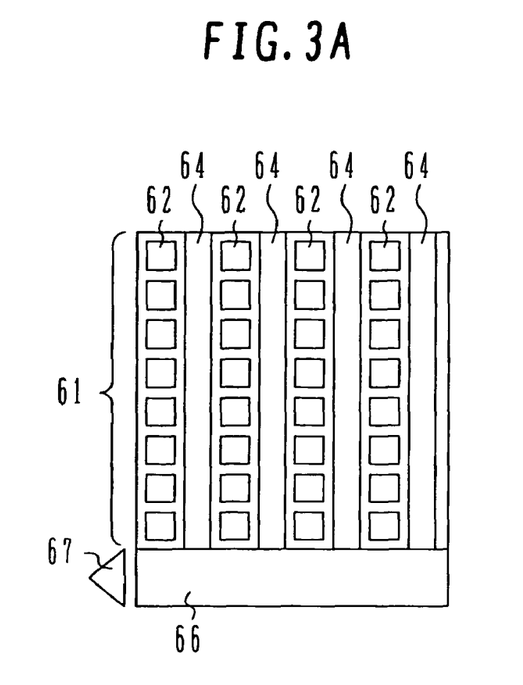
FIGS. 3A and 3B are schematic plan views showing the structure of CCD solid state image pickup devices.
Figure 3B:
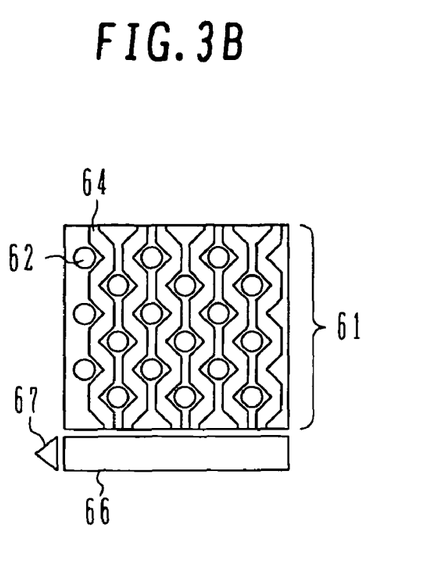
Figure 3C:
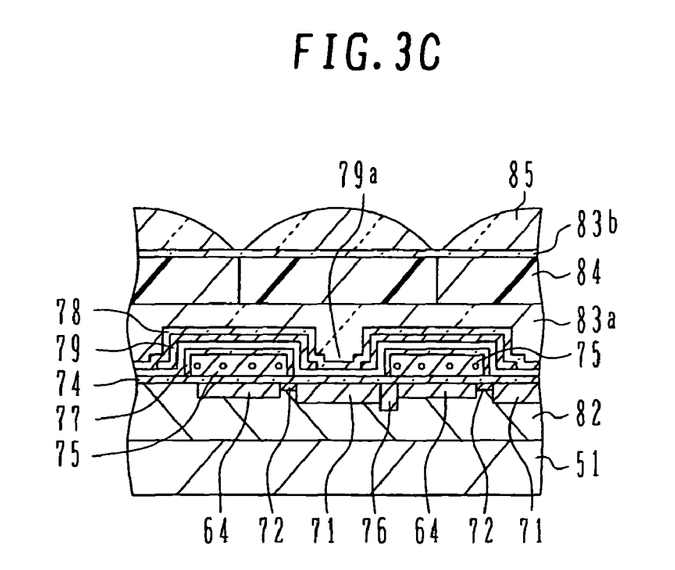
FIG. 3C is a schematic cross sectional view showing a partial region of a light reception region of a CCD solid state image pickup device.

With reference to FIGS. 3A to 3C, the main functional portions of a silicon substrate will be described. FIGS. 3A and 3B are schematic plan views showing the structure of CCD solid state image pickup devices, and FIG. 3C is a schematic cross sectional view showing a partial region of a light reception region of a CCD solid state image pickup device.

Reference is made to FIG. 3A. A CCD solid state image pickup device is constituted of: a plurality of photosensitive regions 62 disposed, for example, in a square matrix shape; a plurality of vertical transfer channels (vertical CCDs) 64 disposed along columns of the photosensitive regions 62; a horizontal transfer channel (horizontal CCD) 66 electrically connected to the ends of the vertical transfer channels 64 outside a light reception region (pixel array region) 61; and a charge detection unit 67 coupled to one end of the horizontal transfer channel 66. The light reception region 61 is constituted of the photosensitive regions 62 and vertical transfer channels 64.

The photosensitive region 62 is constituted of a photosensitive element, e.g., a photodiode, and a transfer gate. The photodiode generates and accumulates signal charges corresponding to an incidence light amount. The accumulated signal charges are read to the vertical transfer channels 64 via transfer gates and transferred in the vertical transfer channels 64 along a direction (vertical direction, column direction) toward the horizontal transfer channel 66 as a whole. Signal charges transferred to the ends of the vertical transfer channels 64 are transferred into the horizontal transfer channel 66.

Signal charges transferred into the horizontal transfer channel 66 are transferred in the horizontal transfer channel 66 along a direction crossing the vertical direction as a whole, e.g., a horizontal direction (direction perpendicular to the vertical direction, row direction), and thereafter transferred to the charge detection unit 67. In accordance with the signal charges transferred from the horizontal transfer channel 66, the charge detection unit 67 performs charges-voltage conversion and signal amplification. The amplified image signal is delivered to an external.

The array of photosensitive regions 62 includes a square array and a rectangle array with the photosensitive regions being disposed along the row and column directions at constant pitches as shown in FIG. 3A, and in addition, a pixel interleaved array (PIA) having pixels disposed along the row and column directions by shifting the pixels, for example, a half pitch at every second rows and columns.

FIG. 3B is a schematic plan view of a CCD solid state image pickup device of the pixel interleaved array. The pixel interleaved array is an array of photosensitive regions disposed in a first square matrix shape and photosensitive regions disposed in a second square matrix shape at positions between lattice points of the first square matrix shape. The vertical transfer channel 64 is formed in a zigzag shape between photosensitive regions 62. Also in this case, signal charges are transferred in the vertical transfer channel 64 along a direction (vertical direction) toward the horizontal transfer channel 66 as a whole. the photosensitive region 62 in the pixel interleaved array is of an octagonal shape in many cases.

FIG. 3C is a schematic cross sectional view showing a partial region of the light reception region of a CCD solid state image pickup device. For example, formed in a p-type well 82 formed in an n-type silicon substrate 51 are a charge accumulation region 71 made of an n-type impurity doped region and a vertical transfer channel 64 made of an n-type impurity region being adjacent to a plurality of charge accumulation regions and via a p-type transfer gate 72. A photodiode is constituted of the n-type charge accumulation region 71 and underlying p-type well 82.

A vertical transfer electrode 75 is formed above the transfer gate 72 and vertical transfer channel 64, with an insulating film 74 being interposed therebetween. A p-type channel stopper region 76 is formed between adjacent charge accumulation regions 71.

The channel stop region 76 electrically isolates the charge accumulation region 71, vertical transfer channel 64 and the like. The insulating film 74 is, for example, a lamination structure (ONO film) of an oxide film, a nitride film and an oxide film, formed on the surface of the silicon substrate 51. The vertical transfer electrode 75 includes a first vertical transfer electrode and a second vertical transfer electrode made of, for example, polysilicon. These electrodes may be made of amorphous silicon. The vertical transfer electrode 75 controls the potentials of the vertical transfer channel 64 and transfer gate 72 to read charges accumulated in the charge accumulation region 71 to the vertical transfer channel 64 and transfer the read charges in the vertical transfer channel 64 along the column direction.

An insulating silicon oxide film 77 formed, for example, by thermally oxidizing polysilicon is formed on the vertical transfer electrode 75.

A light shielding film 79 made of, for example, tungsten (W), is formed above the vertical transfer electrode 75 via the insulating silicon oxide film 77 and an insulating film of silicon oxide, silicon nitride or the like formed on the whole substrate surface by CVD or the like. An opening 79*a* is formed through the light shielding film 79 above the charge accumulation region 71. The light shielding film 79 prevents incidence light upon the light reception region 61 from entering the region other than the charge accumulation region 71. A silicon nitride film 78 is formed on the light shielding film 79.

A planarizing layer 83*a* made of, for example, borophosphosilicate glass (BPSG) is formed above the light shielding film 79. A color filter layer 84 of, e.g., three primary colors of red (R), green (G) and blue (B) is formed on the flat surface of the planarizing layer. In order to planarize the upper surface of the color filter layer, another planarizing layer 83*b* is formed. Micro lenses 85 are formed on a flat surface of the planarizing layer 83*b*, for example, by melting and solidifying a micro lens photoresist pattern. The micro lenses 85 are an array of, e.g., fine semispherical convex lenses disposed above the charge accumulation regions 71. Each micro lens 85 converges incidence light on the charge accumulation region 71. Light converged by each micro lens passes through the color filter layer 84 of one of red (R), green (G) and blue (B) and becomes incident upon the corresponding charge accumulation region (photodiode) 71. A plurality of photodiodes include therefore three types of photodiodes: a photodiode upon which light transmitted through the red (R) color filter layer 84 becomes incident; a photodiode upon which light transmitted through the green (G) color filter layer 84 becomes incident; and a photodiode upon which light transmitted through the blur (B) color filter layer 84 becomes incident.

Signal charges accumulated in the charge accumulation region 71 and corresponding in amount to an incidence light amount are read to the vertical transfer channel 64 by a drive signal (read voltage) applied to the vertical transfer electrode 75 above the transfer gate 72, and transferred in the vertical transfer channel 64 by a drive signal (transfer voltage) applied to the vertical transfer electrode 75.

With reference to FIGS. 4A to 4D, description will be made on a peripheral area (the input/output protective circuit and the like under the shield layer 90) of the silicon substrate and the spacer 55.

Figure 4A:
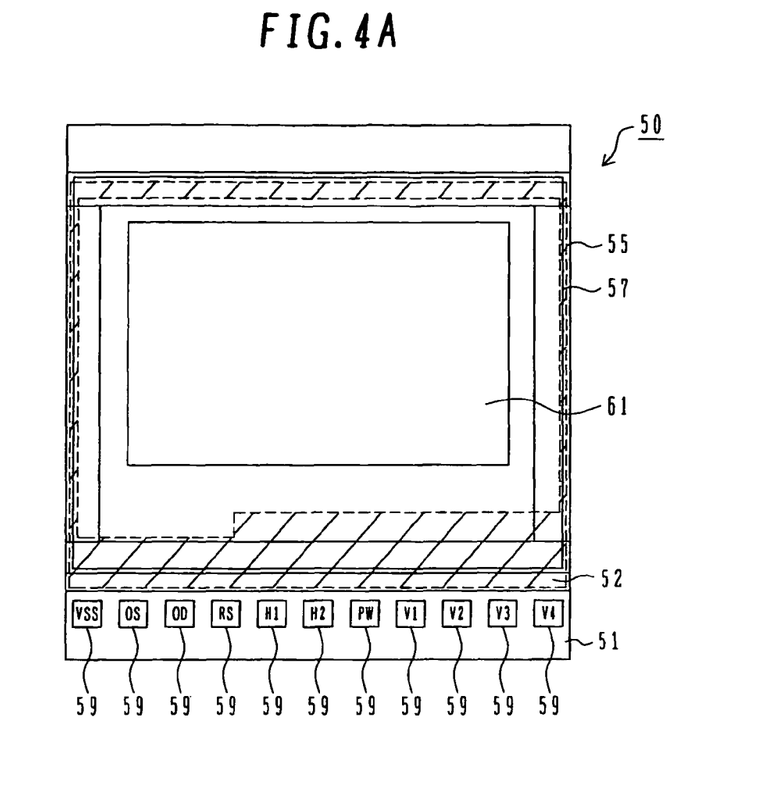
FIGS. 4A to 4D are diagrams illustrating a peripheral area (an input/output protective circuit and the like under a shield layer 90) of a silicon substrate and a spacer 55.

Reference is made to FIG. 4A. In FIG. 4A, an area of the silicon substrate where a peripheral circuit is formed is surrounded by a broken line and hatched.

For example, an input/output protective circuit is formed in a large area and only a portion thereof exists under the spacer in some cases.

A plurality of pads 59 to be used for connection to an external wiring substrate include a supply voltage terminal (ground terminal) VSS, an output voltage terminal OS, a supply voltage terminal OD, a reset pulse voltage terminal RS, horizontal transfer electrode drive signal terminals H1 and H2, a protector/well voltage terminal PW and vertical transfer electrode drive signal terminals V1 to V4.

Of these terminals, VSS, OD and PW are not provided with a protective circuit, whereas V1 to V4 are connected to PW via a protective circuit and H1, H2 and RS are connected to VSS via a protective circuit.

Figure 4B:
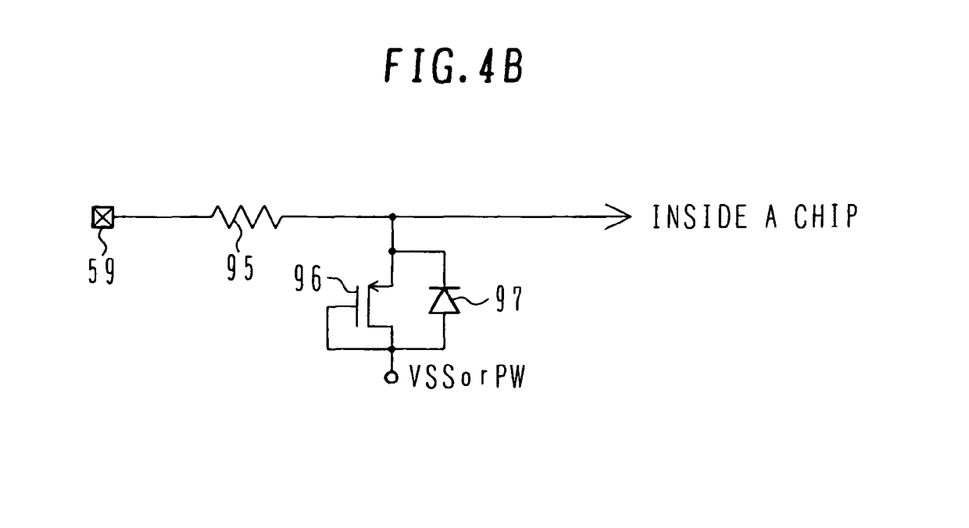

FIG. 4B is an equivalent circuit of the protective circuit. A pad 59 is electrically connected to a solid state image pickup device via a protective resistor 95, and to a VSS or PW pad 59 via a parallel circuit of a metal gate transistor 96 and a diode 97, between the protective resistor and solid state image pickup device.

In the protective circuit shown in FIG. 4B, for example, when a negative surge voltage is input from the pad 59, the diode 97 turns on so that the surge voltage is absorbed in VSS or PW and the circuit in the solid state image pickup device can be protected. When a positive surge voltage is input, the metal gate field transistor 96 turns on so that the surge voltage is absorbed in VSS or PW and the circuit in the solid state image pickup device can be protected.

Figure 4C:
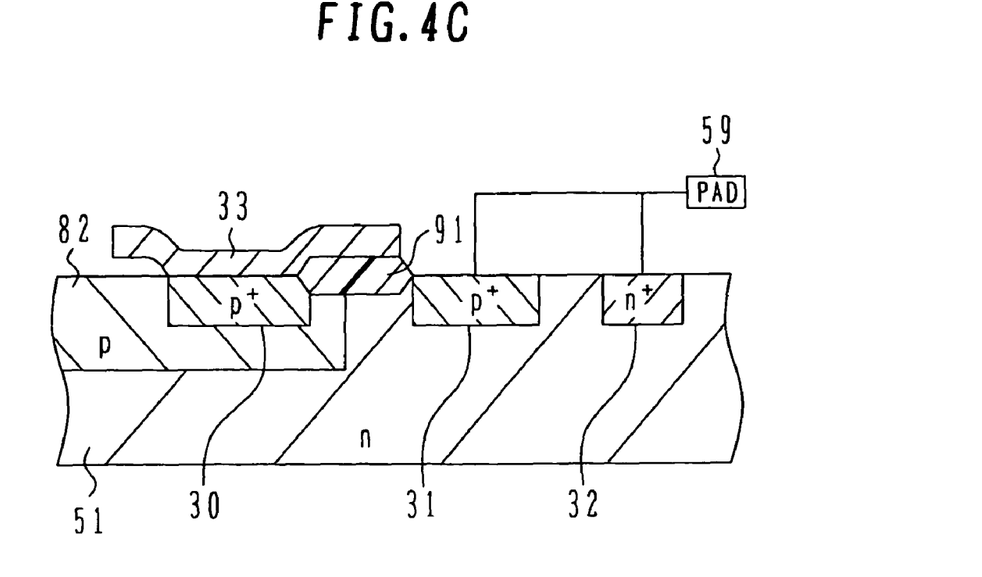

FIG. 4C shows an embodiment of the protective circuit shown in FIG. 4B. An $SiO_2$ layer (isolation region) 91 is formed on the surface of an n-type silicon substrate 51. A p-type well 82 having an edge defined under the $SiO_2$ layer 91 is formed in the surface layer of the silicon substrate 51. A high concentration p-type impurity layer 30 is formed in the p-type well 82 on one side of the $SiO_2$ layer 91, and a drain/gate electrode 33 is formed on the high concentration p-type impurity layer 30 and $SiO_2$ layer 91.

A high concentration p-type impurity layer 31 is formed in the surface layer of the silicon substrate 51 on the other side of the $SiO_2$ layer 91 opposite to the high concentration p-type impurity layer 30. A high concentration n-type impurity layer 32 is formed in the surface layer of the silicon substrate 51. The high concentration p-type impurity layer 31 and high concentration n-type impurity layer 32 are connected in common to the pad 59.

The high concentration n-type impurity layer 32, n-type silicon substrate 51 and p-type well 82 constitute the diode 97. The metal gate field transistor 96 is formed by using the high concentration p-type impurity layer 31 as a source, the high concentration p-type impurity layer 30 and p-type well 82 as a drain, the n-type region under the $SiO_2$ layer 91 as a channel and the electrode on the $SiO_2$ layer 91 as a gate.

Figure 4D:
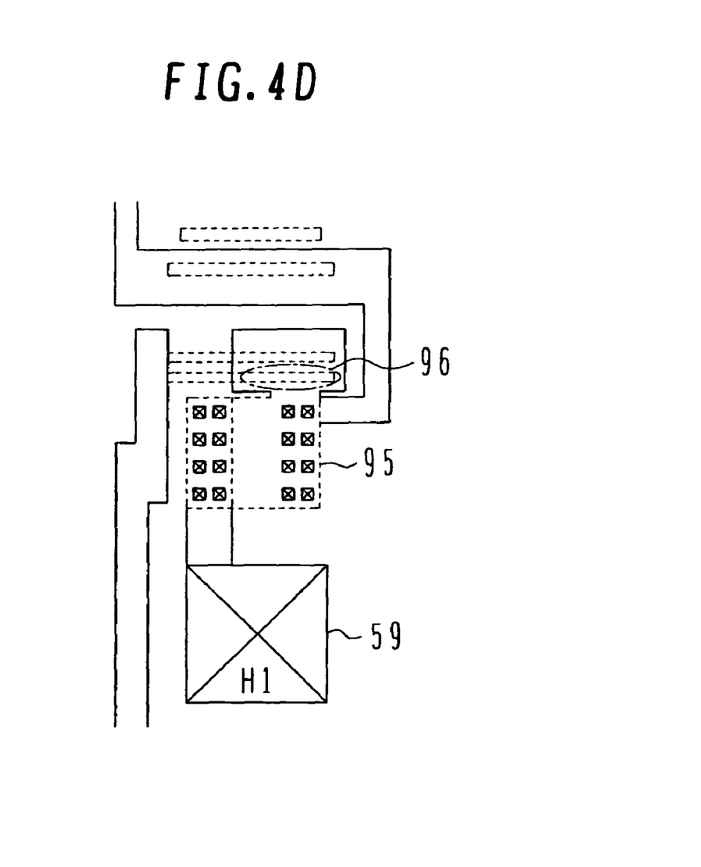

Reference is made to FIG. 4D. FIG. 4D shows an example of the protective circuit near the pad 59 H1 shown in FIG. 4A. The protective circuit is constituted of the protective resistor 95 and metal gate field transistor 96 shown in FIG. 4B. The shield layer and spacer are formed, for example, above the metal gate field transistor 96 of the protective circuit 96 to protect the protective circuit from electrostatic breakage.

Figure 5A:
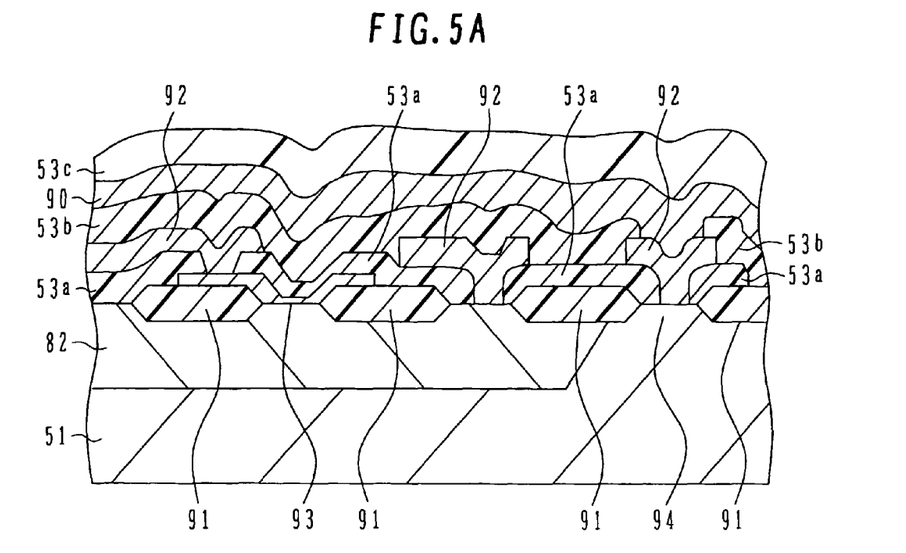
FIGS. 5A and 5B are schematic cross sectional views showing the region near the shield layer 90.
Figure 5B:
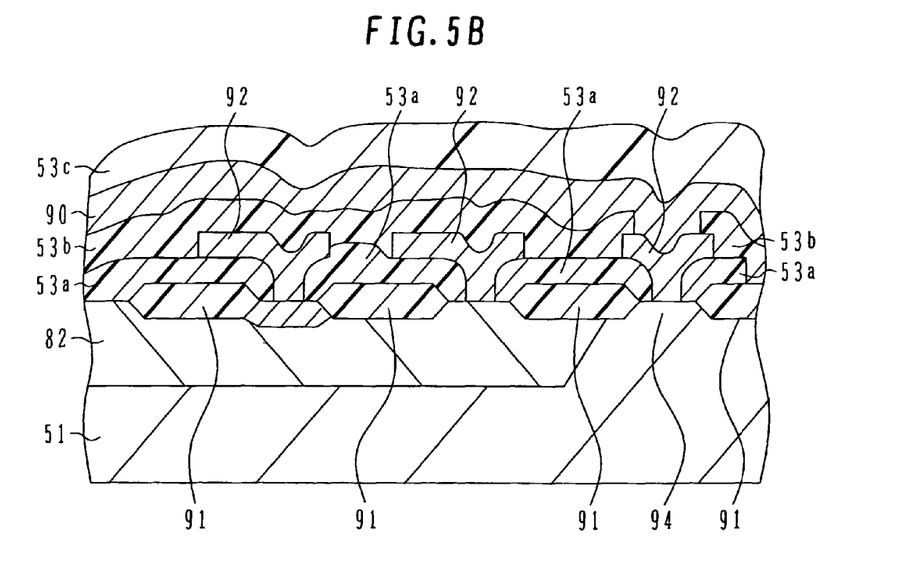

FIGS. 5A and 5B are schematic cross sectional views showing the region near the shield layer 90. FIG. 5A is a cross sectional view showing the region with the polysilicon layer constituting the gate electrode, and FIG. 5 is a cross sectional view showing the region with the source/drain Al electrode instead of the gate electrode.

Reference is made to FIG. 5A. A peripheral circuit of a semiconductor device, e.g., the input/output protective circuit described with reference to FIGS. 4B to 4D, is formed in a p-type well 82 formed in a surface layer of an n-type silicon substrate 51. The peripheral circuit is formed in the p-type well 82 in the light reception region of a solid state image pickup device and a peripheral area of the horizontal CCD.

An SiO$_2$ layer (isolation region) 91 as an insulating layer is formed on the surface of the well layer 82. In an active region defined by the SiO$_2$ layer 91, an Al layer 92 constituting a source/drain electrode and a polysilicon layer 93 constituting a gate electrode are formed. The Al layer 92 is electrically connected to the well 82 to form a well contact.

A shield layer 90 made of, for example, Al is formed above the Al layer 92. The shield layer 90 is electrically connected to the n-type silicon substrate 51 at a position where the well 82 is not formed, to form a substrate contact 94. A passivation film 53a is used for electrical insulation of the gate electrode, and a passivation film 53b is used for electrical insulation of the Al layer 92.

A passivation film 53c is formed on the shield layer 90, and a spacer is formed above the passivation film.

Reference is made to FIG. 5B. Similar to the structure shown in FIG. 5A, the shield layer 90 is made conductive with the silicon substrate 51.

By adopting this structure, even if static electricity is generated on the surface of the protective glass and a high voltage is generated on the bottom surface of the spacer during a bonding process for the spacer and protective glass, during a bonding process for the spacer semiconductor device, during a dicing process or during other processes, this voltage can be absorbed. Namely, this voltage is applied not to the device but to the shield layer electrically connected to the silicon substrate. This voltage can be applied to an external of the semiconductor chip via the shield layer 90 and silicon substrate 51. It is therefore possible to protect the semiconductor device (input/output protective circuit, wiring portion and the like) from electrostatic breakdown. A solid state image pickup device having a high static electricity resistance and high quality can therefore be realized even if "the structure that a protective glass is disposed only in the light reception region", which is advantageous in compactness of a semiconductor chip, is adopted.

The shield layer 90 may be made of the same metal layer as that of the light shielding film 79 shown in FIG. 2C.

A compact and high quality endoscope can be realized by using the above-described solid state image pickup device.

Figure 6A:
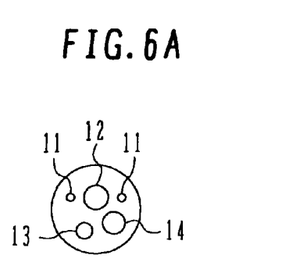
FIG. 6A is a schematic plan view showing a tip portion of an upper digestive tract fine inspection optical magnification electron scope (endoscope)
Figures 6B, 6D:
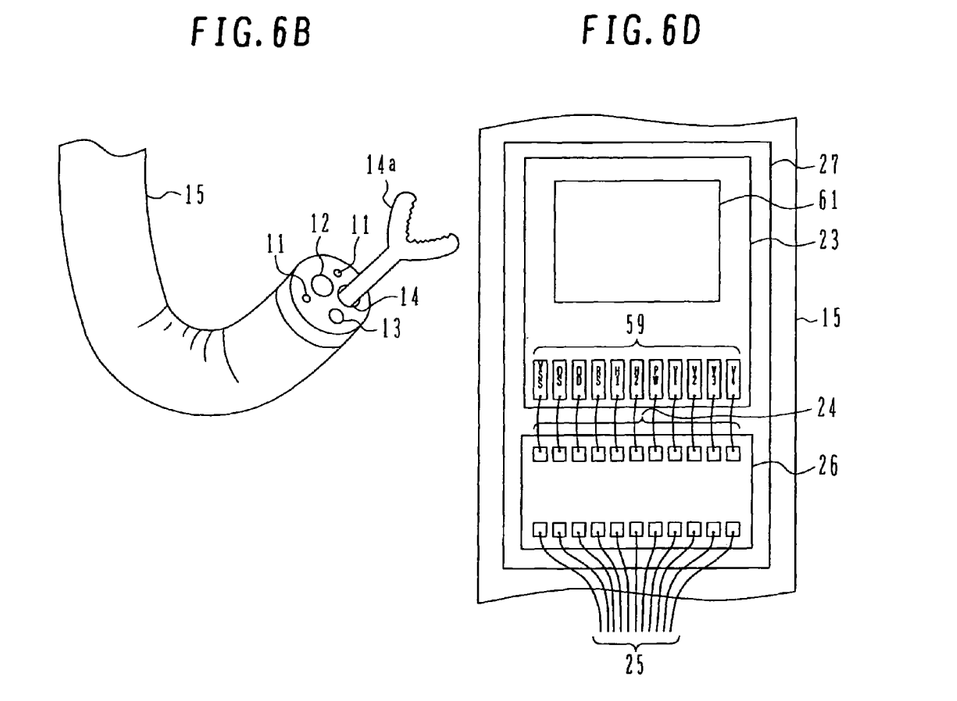
FIG. 6B is a perspective view of the tip portion of the scope and a tube near the tip portion.
FIGS. 6C and 6D are schematic diagrams illustrating an observation optical system of the scope.
Figure 6C:
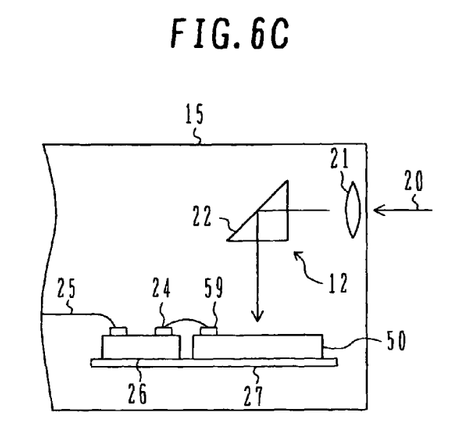

FIG. 6A is a schematic plan view showing a tip portion of an upper digestive tract fine inspection optical magnification electron scope (endoscope), FIG. 6B is a perspective view of the tip portion of the scope and a tube near the tip portion, and FIGS. 6C and 6D are schematic diagrams illustrating an observation optical system of the scope.

Reference is made to FIG. 6A. The tip portion of an upper digestive tract fine inspection optical magnification electron scope (endoscope) has generally a circular shape of 6.0 mm diameter and is constituted of a light source 11, an observation optical system 12, a nozzle 13 and a forceps opening 14. The light source 11 shown in FIG. 6A corresponds to an outlet port for the light source including a light emission source, a light guide (fiber) and the outlet port. The electron scope is used, for example, as a photogastroscope.

The light source 11 is formed at two positions of the tip portion, emits, for example, white light whose infrared range is cut, and illuminates an organism such as a human gaster wall. The observation optical system 12 is constituted of a solid state image pickup device like the embodiment solid state image pickup device, forms an image mainly by receiving light emitted from the light source and reflected from the gaster wall, and transmits the image to an observer. The observation optical system 12 will be later detailed. The nozzle 13 is an output port which jets out air or liquid, for example, wash or stain. The forceps opening 14 is an inlet/outlet port of forceps. The forceps opening has a diameter of, for example, 2.8 mm.

Reference is made to FIG. 6B. A pair of forceps 14a is pulled out or in through the forceps opening 14. The forceps 14a perform an open/close operation at its tip portion like blades of a pair of scissors, and can grip or squeeze an object. By operating the forceps 14a, it is possible to observe a disease portion in detail and pick up cells of the disease portion.

The light source (outlet port) 11, observation optical system 12, nozzle 13 and forceps opening 14 (forceps 14a) are disposed in the tube 15, e.g., near at the tip portion of the tube. The tube 15 is introduced into the body via, for example, a nose nostril to make the tip portion reach near the disease portion. If the tube is introduced not via a mouse but via a nose nostril, a patient can be inspected while a conversation with the patient is made. A scope to be introduced via a nose nostril has a small diameter than that of a scope to be introduced via a mouse.

A portion near the tip portion of the tube 15 is made flexible so that the operation of the scope such as moving the observation optical system 12 and the like nearer to the disease portion can be improved. A total length of the tube 15 is, for example, 1400 mm. The tube 15 is provided with a control device at the end of the tube opposite to the position where the observation optical system 12 and the like are disposed. The control device can operate the light source 11, observation optical system 12, nozzle 13 and forceps 14a. Image data from the observation optical system 12 is transmitted in the tube 15 to an external. The tube 15 is a mechanical and electrical transmission tube.

With reference to FIG. 6C, the observation optical system 12 will be described. The observation optical system 12 is constituted of an objective lens 21, a prism 22, a semiconductor chip 50 and a wiring substrate 26. Light 20 emitted from the light source 11 and reflected from, for example, a gaster wall, becomes incident upon the objective lens 21, changes its propagation direction to a right angle direction at the prism 22 which is an optical path changing device installed above the solid state image pickup device, and becomes incident upon the semiconductor chip 50.

The embodiment solid state image pickup device and pads 59 are formed on the semiconductor chip 50. Pads 24 of the wiring substrate 26, on which wirings such as those of a drive circuit are formed, are wire-bonded to the pads 59 of the semiconductor chip 50. Leads 25 from the wiring substrate 26 extend in the tube 15 along the extension direction of the tube 15. The semiconductor chip 50 and wiring substrate 26 are supported on a support plate 27.

Reference is made to FIG. 6D. Light 20 incident upon the objective lens 21 being changed its propagation direction by the prism 22 becomes incident upon a plurality of photoelectric conversion elements in the light reception region 61 of the solid state image pickup device of the semiconductor chip 50 so that signal charges are generated and accumulated. After the signal charges are transferred in the solid state image pickup device, the charges are output as image data. The image data is output to an external via leads 25.

The semiconductor chip 50 is disposed in such a manner that its principal surface (surface on which the photoelectric conversion elements are formed) of, e.g., a rectangular shape, is perpendicular to the cross section of the tube 15 and a longitudinal direction of the principal surface is parallel to the extension direction of the tube 15. With this arrangement, the scope can be made compact. Changing the propagation direction of incidence light by the prism 22 is intended to make the scope compact by disposing the principal surface of the semiconductor chip 50 perpendicular to the cross section of the tube 15.

The semiconductor chip 50 is disposed in such a manner that its upper side (on the side of the light reception region 61) is positioned near to the objective lens 21. Therefore, light to become incident upon the objective lens 21 before the light is reflected by the prism 22 propagates along a direction from the light reception region 61 toward the horizontal transfer channel and pads 59 (in a direction of transferring signal charges in the vertical transfer channel in the light reception region 61 as a whole).

Since the endoscope shown in FIGS. 6A to 6D uses the embodiment solid state image pickup device, the endoscope is compact and has a high static electricity resistance and high quality.

Although a medical endoscope is shown in FIGS. 6A to 6D, an industrial endoscope can be realized which is compact and has a high static electricity resistance and high quality.

The present invention is particularly suitable for application to a solid state image pickup device and an endoscope to be used for the fields where compactness requirements are severe.

The present invention has been described in connection with the preferred embodiments. The invention is not limited only to the above embodiments. It will be apparent to those skilled in the art that other various modifications, improvements, combinations, and the like can be made.

I claim:

1. A solid state image pickup device comprising:
   a semiconductor substrate of a first conductivity type;
   a well of a second conductivity type opposite to the first conductivity type formed in a surface layer of said semiconductor substrate;
   a light reception region formed in said well and including a plurality of charge accumulation regions of the first conductivity type formed in a matrix shape for accumulating signal charges generated in correspondence with an amount of incidence light and a plurality of vertical CCDs formed along each column of said charge accumulation regions for reading the signal charges accumulated in said charge accumulation regions and transferring the signal charges in a column direction;
   a horizontal CCD formed in said well and coupled to ends of said vertical CCDs for transferring the signal charges transferred from said vertical CCDs;
   a peripheral circuit formed in said well in partial regions of said light reception region and said horizontal CCD;
   a shield layer formed on said semiconductor substrate including a partial area above said peripheral circuit, made of conductive material and surrounding said light reception region, said shield layer being electrically connected to said semiconductor substrate of the first conductivity type and being in contact with the semiconductor substrate of the first conductivity type;
   a support disposed on said shield layer through an insulating layer and made of conductive material, and
   a translucent member placed on said support.

2. The solid state image pickup device according to claim 1, wherein said shield layer is made of aluminum or alloy of copper or silicon containing aluminum as a main component.

3. The solid state image pickup device according to claim 1, further comprising a light shielding film having an opening above each of said charge accumulation regions of said light reception region.

4. The solid state image pickup device according to claim 3, wherein said light shielding film is made of tungsten.

5. The solid state image pickup device according to claim 3, wherein said shield layer is made of a same metal layer as a metal layer of said light shielding film.

6. The solid state image pickup device according to claim 1, wherein said charge accumulation regions disposed in the matrix shape include first charge accumulation regions disposed in a first square matrix shape and second charge accumulation regions disposed in a second square matrix shape at positions between lattice points of the first charge accumulation regions disposed in the first square matrix shape.

7. The solid state image pickup device according to claim 1, wherein said first conductivity type is an n-type.

8. The solid state image pickup device according to claim 1 wherein the shield layer is in direct physical contact with the substrate of the first conductivity type.

9. The solid state image pickup device according to claim 1 wherein the shield layer and the substrate of the first conductivity type are at substantially the same potential.

10. The image pickup device of claim 1, wherein the peripheral circuit is disposed at a distance of 2 μm to 10 μm from a top surface of the shield layer.

11. An endoscope comprising:
    a light source for emitting light;
    a solid state image pickup device including a semiconductor substrate of a first conductivity type, a well of a second conductivity type opposite to the first conductivity type formed in a surface layer of said semiconductor substrate, a light reception region formed in said well and including a plurality of charge accumulation regions of the first conductivity type formed in a matrix shape for accumulating signal charges generated in correspondence with an amount of incidence light and a plurality of vertical CCDs formed along each column of said charge accumulation regions for reading the signal charges accumulated in said charge accumulation regions and transferring the signal charges in a column direction, a horizontal CCD formed in said well and coupled to ends of said vertical CCDs for transferring the signal charges transferred from said vertical CCDs, a peripheral circuit formed in said well in partial regions of said light reception region and said horizontal CCD, a shield layer formed on said semiconductor substrate including a partial area above said peripheral circuit, made of conductive material and surrounding said light reception region, said shield layer being electrically connected to said semiconductor substrate of the first conductivity type and being in contact with the semiconductor substrate of the first conductivity type, a support disposed on said shield layer through an insulating layer and made of conductive material, and a translucent member placed on said support; and
    a transmission tube having therein said light source and said solid state image pickup device.

12. The endoscope according to claim 11, wherein said shield layer is made of aluminum or alloy of copper or silicon containing aluminum as a main component.

13. The endoscope according to claim 11, further comprising a light shielding film having an opening above each of said charge accumulation regions of said light reception region.

14. The endoscope according to claim 13, wherein said light shielding film is made of tungsten.

15. The endoscope according to claim 13, wherein said shield layer is made of a same metal layer as a metal layer of said light shielding film.

16. The endoscope according to claim 11, wherein said charge accumulation regions disposed in the matrix shape include first charge accumulation regions disposed in a first square matrix shape and second charge accumulation regions disposed in a second square matrix shape at positions between lattice points of the first charge accumulation regions disposed in the first square matrix shape.

17. The endoscope according to claim 11, wherein the first conductivity type is an n-type.

18. The endoscope according to claim 11, wherein said light source emits white light whose infrared range is cut.

19. The endoscope according to claim 11, further comprising a jetting device provided in said transmission tube for jetting out gas or liquid.

20. The endoscope according to claim 11, further comprising an operation device capable of squeezing an object provided in said transmission tube, said operation device being capable of being pulled in or out through an opening formed in said transmission tube.

* * * * *